(12) United States Patent
Miller et al.

(10) Patent No.: US 11,331,462 B2
(45) Date of Patent: May 17, 2022

(54) DEVICE, DISPENSING APPARATUS AND METHODS FOR ADMINISTERING COLLAGEN MODIFIER COMPOUNDS

(71) Applicant: Advanced Collagen Science LLC, Brookline, MA (US)

(72) Inventors: Leonard B. Miller, Brookline, MA (US); Dale P. Devore, Chelmsford, MA (US)

(73) Assignee: Advanced Collagen Science LLC, Brookline, MA (US)

( * ) Notice: Subject to any disclaimer, the term of this patent is extended or adjusted under 35 U.S.C. 154(b) by 528 days.

(21) Appl. No.: 16/463,155

(22) PCT Filed: Nov. 22, 2017

(86) PCT No.: PCT/US2017/063101
§ 371 (c)(1),
(2) Date: May 22, 2019

(87) PCT Pub. No.: WO2018/098346
PCT Pub. Date: May 31, 2018

(65) Prior Publication Data
US 2019/0374760 A1 Dec. 12, 2019

Related U.S. Application Data

(60) Provisional application No. 62/426,007, filed on Nov. 23, 2016.

(51) Int. Cl.
*A61M 37/00* (2006.01)

(52) U.S. Cl.
CPC .... *A61M 37/0015* (2013.01); *A61M 37/0092* (2013.01); *A61M 2037/0007* (2013.01); *A61M 2037/0023* (2013.01); *A61M 2037/0061* (2013.01); *A61M 2205/6018* (2013.01)

(58) Field of Classification Search
CPC .......... A61M 37/0015; A61M 37/0092; A61M 2037/0007; A61M 2037/0023; A61M 2037/0061; A61M 2205/6018
USPC ...................................................... 604/506
See application file for complete search history.

(56) References Cited

U.S. PATENT DOCUMENTS

| 5,848,991 | A | * | 12/1998 | Gross | ............... | A61M 5/14593 |
| | | | | | | 604/140 |
| 7,226,439 | B2 | * | 6/2007 | Prausnitz | ........... | A61B 5/14514 |
| | | | | | | 604/506 |
| 2006/0078591 | A1 | | 4/2006 | Del Vecchio | | |
| 2009/0169615 | A1 | | 7/2009 | Pinsky | | |
| 2013/0144261 | A1 | | 6/2013 | Chowdhury | | |
| 2016/0038391 | A1 | * | 2/2016 | Miller | ................... | A61K 8/498 |
| | | | | | | 514/460 |

OTHER PUBLICATIONS

International Search Report and Written Opinion for Application No. PCT/US2017/063101, dated Jan. 26, 2018, 10 pages.

\* cited by examiner

*Primary Examiner* — Phillip A Gray
(74) *Attorney, Agent, or Firm* — Unikel Law LLC

(57) ABSTRACT

Embodiments of the present invention are directed to devices and apparatus for administering collagen modifier compounds to the dermis of skin.

26 Claims, 3 Drawing Sheets

DEVICE, DISPENSING APPARATUS AND METHODS FOR ADMINISTERING COLLAGEN MODIFIER COMPOUNDS

This application is a U.S. national stage filing under 35 U.S.C. § 371 based on International Application No. PCT/US2017/063101, filed Nov. 22, 2017, which claims priority to U.S. Provisional Application No. 62/426,007, filed Nov. 23, 2016. The entire contents of each of the aforementioned applications are incorporated herein by reference.

STATEMENT REGARDING FEDERAL FUNDING

Embodiments of the present invention were not conceived or reduced to practice with Federal funds or sponsorship.

FIELD OF THE INVENTION

Embodiments of the present invention are directed to devices, dispensing apparatus and methods for administering collagen modifier compounds, such as by way of example, without limitation, acetylation agents, including, without limitation, glutaric anhydride.

BACKGROUND OF THE INVENTION

Aging is accompanied by changes in the skin. The skin loses elasticity, hydration and pigmentation. The dermal layer exhibits atrophy and fewer fibroblasts, vessels and mast cells, shorter capillary loops and abnormal nerve endings. The dermal volume may be reduced by twenty percent.

It is useful to modify collagen to restore hydration and elasticity lost through aging and other processes. A number compounds are known to be able to modify or react with collagen. These compounds, acetylation agents, are difficult to administer. The compounds react with molecules other than collagen.

Collagen is a structural component of the dermis. In order to administer collagen modifier compounds to the skin, the modifier compounds must transit through the outer epidermis layer. The epidermis is a significant barrier for molecules which are reactive.

SUMMARY OF THE INVENTION

Embodiments of the present invention are directed to devices and methods for administering collagen modifier compounds past the epidermis and into the collagen of the dermis. One embodiment directed to a device, for administering a collagen modifier compound, comprises injection means, a first compartment, a second compartment, communication means, a collagen modifier compound, and a reconstitution liquid. The injection means is for receiving a collagen modifier compound in a hydrated formulation and transporting the hydrated formulation to a collagen site across the epidermal layer of the skin to react with endogenous collagen of the dermis. The injection means has a sheet having an administration side, a formulation side and openings. The administration side has one or more needles in communication with the openings for transporting a hydrated formulation to the collagen site. The formulation side forms a first compartment or is in fluid communication with a first compartment. The first compartment is for holding a hydrated formulation and at least one of a collagen modifier compound and a reconstitution liquid. The first compartment is in fluid communication with the openings or constructed and arranged to form communication with the openings. The second compartment is for holding at least one of a collagen modifier compound, a reconstitution liquid and a hydrated formulation. At least one of the first compartment and second compartment is collapsible to propel a hydrated formulation through the openings. The communication means is for placing the first compartment in fluid communication with the second compartment to allow a collagen modifier compound to become hydrated with a reconstitution liquid to form a hydrated formulation for administration. The collagen modifier compound held in one of said first compartment and said second compartment. The reconstitution liquid is held in one of said first compartment and said second compartment not holding said collagen modifier compound. The collagen modifier compound and reconstitution liquid form a hydrated formulation upon activation communication means. The injection means is for placing openings proximal to a collagen site upon pressing the administration side against the skin, and the at least one of the first compartment and second compartment for collapsing propelling hydrated formulation to the collagen site.

As used herein, the term "collagen modifier compound" refers to acetylation agents which are reactive with a natural dermal collagen. Although the singular term, "compound" is used, the term is used with the understanding that more than one compound that modifies collagen may be used and such compound may have other constituents to improve its stability and/or formation of a hydrated formulation. The term "natural dermal collagen" refers to a collagen as it is normally and naturally found in the dermis layer of skin. A "modified collagen" refers to a collagen that has reacted with an acetylation agent and bears a higher net charge density due to the modification than the normal natural collagen. As used herein, an "acetylation agent" is a compound that transfers an acyl group to another nucleophile. Examples of acetylation agent include, without limitation, sulfonic acids, anhydrides, sulfonyl chlorides and acid chlorides. The acetylation agent includes compounds such as, without limitation, maleic anhydride, succinic anhydride, glutaric anhydride, citraconic anhydride, methyl succinic anhydride, itaconic anhydride, methyl glutaric anhydride, dimethyl glutaric anhydride, phthalic anhydride, oxalyl chloride, malonyl chloride, chlorosulfonylacetyl chloride, chlorosulfonylbenzoic acid, 4-chloro-3-(chlorosulfonyl)-5-nitrobenzoic acid, 3-sulfobenzoic acid, 3,5-dicarboxybenzenesulfonyl chloride, acetic anhydride, chloroacetic anhydride, propionic anhydride, butyric anhydride, isobutyric anhydride, isovaleric anhydride, hexanoic anhydride, acetyl chloride, propionyl chloride, dichloropropionyl chloride, butyryl chloride, isobutyryl chloride, valeryl chloride, ethane sulfonyl chloride, methane sulfonyl chloride, 1-butane sulfonyl chloride, 4, 6-diamino-2-methylthiopyrimidine-5-sulfonic acid and mixtures and combinations thereof. Several acetylation agents form reaction products with collagen which modify the collagen to increase the hydration of the collagen and/or elasticity of the collagen. The greater hydration of the collagen and/or elasticity of the collagen creates a fullness of the dermis which softens the appearance of lines and wrinkles. One acetylation agent featured in the present application is glutaric anhydride.

As used herein, "communication means" for placing the first compartment in fluid communication with a second compartment is in the nature of a breakable seal or membrane. The communication means separates the reactive collagen modifier compound from the reconstitution liquid. The communication means may further comprise cutters and/or puncture elements, for example, projections protruding from the formulation side of the sheet which disrupt the integrity of the membrane or breakable seal upon flexing or external pressure. Communication means may also work with sonication elements which when activated disrupt the breakable seal and/or membrane.

The reconstitution liquid is in the nature of a sterile solution for injection which upon combining with the collagen modifier compound forms a hydrated formulation. The hydrated formulation holds the collagen modifier compound as a dissolved molecular species. The dissolved molecular species is unstable and needs to be administered within a short period of time. One preferred hydrated formulation comprises 1 to about 100 mg/ml glutaric anhydride in a buffered solution of pH 8 to about pH 10 normal saline.

The term "injection means" refers to one or more micro needles, most preferably constructed and arranged as a plurality of micro needles in an array on a sheet. The sheet provides a base for pressing the microneedle array against the skin. The one or more microneedles of the array are constructed and arranged to administer a dose into the dermis. The length of the microneedle array is about 0.5 mm to about 1.0 mm.

One embodiment of the device features at least one of the first compartment and the second compartment having window means to allow a user to view the hydrated formulation to ensure reconstitution of the collagen modifier compound. For example, without limitation, the first compartment and/or the second compartment is constructed and arranged with a clear plastic portion which allows the hydrated formulation to be viewed and monitored for the presence of undissolved collagen modifier compound.

One embodiment of the device features a pad fixed to the administration side of said sheet. The pad may serve several functions, it may comprise a medicament and/or a skin marker. The medicament is for pretreating skin prior to administration of the hydrated formulation. For example, without limitation, the medicament may comprise conditioning agents, disinfecting agents, numbing agents and agents which render the skin more receptive to the collagen modifier compound. For example, without limitation, one embodiment features a pretreatment agent having a slightly alkaline buffer solution which is applied for 30 seconds to two minutes to bring the tissue pH to about 7.5 to 9.5. The skin marker is a removable dye or coloring agent for marking the outline of the site of administration. As the user of the device, for example, without limitation, a health practitioner or cosmetician or the subject themselves administers the collagen modifier composition in the hydrated formulation, the individual can track the sites of administration to prevent missing locations and reapplication to the same location.

One embodiment features a device wherein the pad is held in a third compartment. One embodiment features a third compartment having means for exposing said pad. For example, without limitation, the third compartment is removable or partially removable to expose the pad or marker element.

One embodiment of the present device features a plurality of devices in a strip for dispensing.

One embodiment further features a device or a plurality of devices received in a dispensing apparatus.

A further embodiment of the present invention is directed to a dispensing apparatus. The dispensing apparatus is constructed and arranged to receive a device, for administering a collagen modifier compound. The device comprises injection means, a first compartment, a second compartment, communication means, a collagen modifier compound, and a reconstitution liquid. The dispensing apparatus prepares the device for administering and/or facilitates the administration of the hydrated formulation. For example, without limitation, one embodiment of the dispensing apparatus has sonication means for promoting the dissolution of the collagen modifier compound.

One embodiment of the dispensing apparatus features compression means for compressing said at least one of said first and second compartments to administer said collagen modifying compound. The compression means may be powered by motors and or solenoid type devices or manually implemented through levers and presses.

One embodiment of the dispensing apparatus has sensing means for determining the dissolution of the collagen modifier compound in the liquid for reconstitution. Upon dissolution, the dispensing apparatus signals to the user that the hydrated formulation is ready by an indicator or manual release of the means for compressing at least one of the first compartment and the second compartment.

One further embodiment of the invention is directed to a method of administering a hydrated formulation comprising the steps of providing a device for administering a collagen modifier compound having injection means, a first compartment, a second compartment, communication means, a collagen modifier compound, and a reconstitution liquid. The injection means is for receiving a collagen modifier compound in a hydrated formulation and transporting the hydrated formulation to a collagen site across the epidermal layer of the skin to react with endogenous collagen of the dermis. The injection means has a sheet having an administration side, a formulation side and openings. The administration side has one or more needles in communication with the openings for transporting a hydrated formulation to the collagen site. The formulation side forms a first compartment or is in fluid communication with a first compartment. The first compartment is for holding a hydrated formulation and at least one of a collagen modifier compound and a reconstitution liquid. The first compartment is in fluid communication with the openings or constructed and arranged to form communication with the openings. The second compartment is for holding at least one of a collagen modifier compound, a reconstitution liquid and a hydrated formulation. At least one of the first compartment and second compartment is collapsible to propel a hydrated formulation through the openings. The communication means is for placing the first compartment in fluid communication with the second compartment to allow a collagen modifier compound to become hydrated with a reconstitution liquid to form a hydrated formulation for administration. The collagen modifier compound held in one of said first compartment and said second compartment. The reconstitution liquid is held in one of said first compartment and said second compartment not holding said collagen modifier compound. The collagen modifier compound and reconstitution liquid form a hydrated formulation for administration through the epidermis upon activation communication means. The injection means is for placing openings proximal to a collagen site upon pressing the administration side against the skin, and the at least one of the first compartment and second compartment for collapsing propelling hydrated formulation to the collagen site. The method further comprises the steps of forming a hydrated formulation by activating the communication means, combining the collagen modifier compound with the reconstitution liquid; pressing the administration side of the sheet on the skin at the site of administration and pressing the one or more needles into the skin; and collapsing the at least one of said first compartment and second compartment to propel said hydrated formulation to the site.

One embodiment of the method features at least one of said first compartment and said second compartment having window means to allow a user to view the hydrated formulation to ensure reconstitution of the collagen modifier compound and further comprises the step of viewing the hydrated formulation prior to propelling the hydrated formulation to the site.

A further embodiment of the method features a pad fixed to the administration side of the sheet wherein said pad has a medicament, said medicament for pretreating skin prior to administration of said hydrated formulation said method comprising the step of pretreating the skin by holding the pad at the site.

One embodiment of the method features a pad held in a third compartment. The third compartment has means for exposing the pad and the method further comprising the step of exposing the pad and pressing the pad against the site to pretreat the site.

One embodiment features a pad or a marking feature on the administration side of the sheet having a skin marker for marking the outline of the site of administration. The method further comprises the step of monitoring the administration by marking the skin. The method further comprises the step of aligning the mark on the skin with a subsequent application of hydrated formulation.

These and other features and advantages will be apparent to those skilled in the art upon viewing the Figures, which are described briefly below, and studying the Detailed Description in the text that follows.

DETAILED DESCRIPTION OF THE INVENTION

Embodiments of the present invention will now be described in detail with respect to a device for administering collagen modifier compounds and dispensing apparatus using such devices and methods associated with their use. Collagen modifier compounds and kits for administering collagen modifier compounds are described in United States Patent Publication Number 2016/0038391, U.S. Ser. No. 14/782,420 to Miller and Devore for "Methods and Articles of Manufacture for the Treatment of Skin", which publication is incorporated by reference in its entirety.

Figure 1:
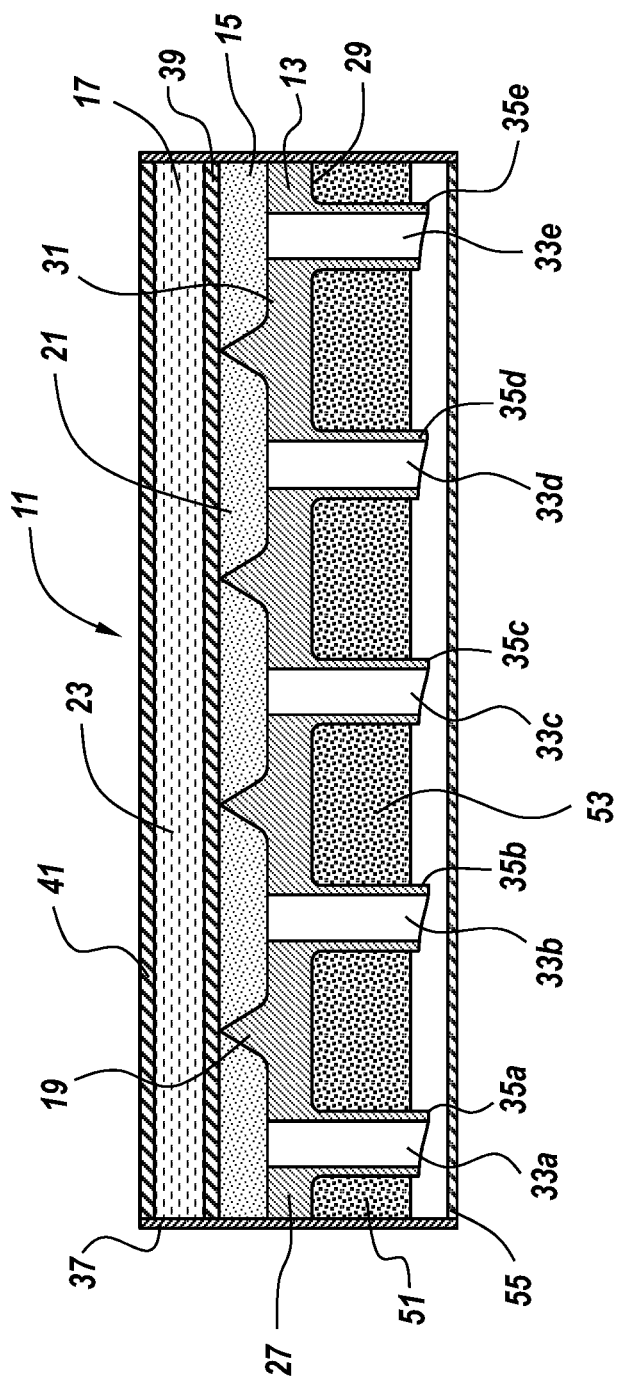
FIG. 1 depicts in cross section a device having features of the present invention.

Turning now to FIG. 1, one embodiment of the present invention is directed to a device for administering collagen modifier compounds past the epidermis and into the collagen of the dermis, generally designated by the numeral 11. Device 11 has the following major elements injection means 13, a first compartment 15, a second compartment 17, communication means 19, a collagen modifier compound 21, and a reconstitution liquid 23.

Figure 2:
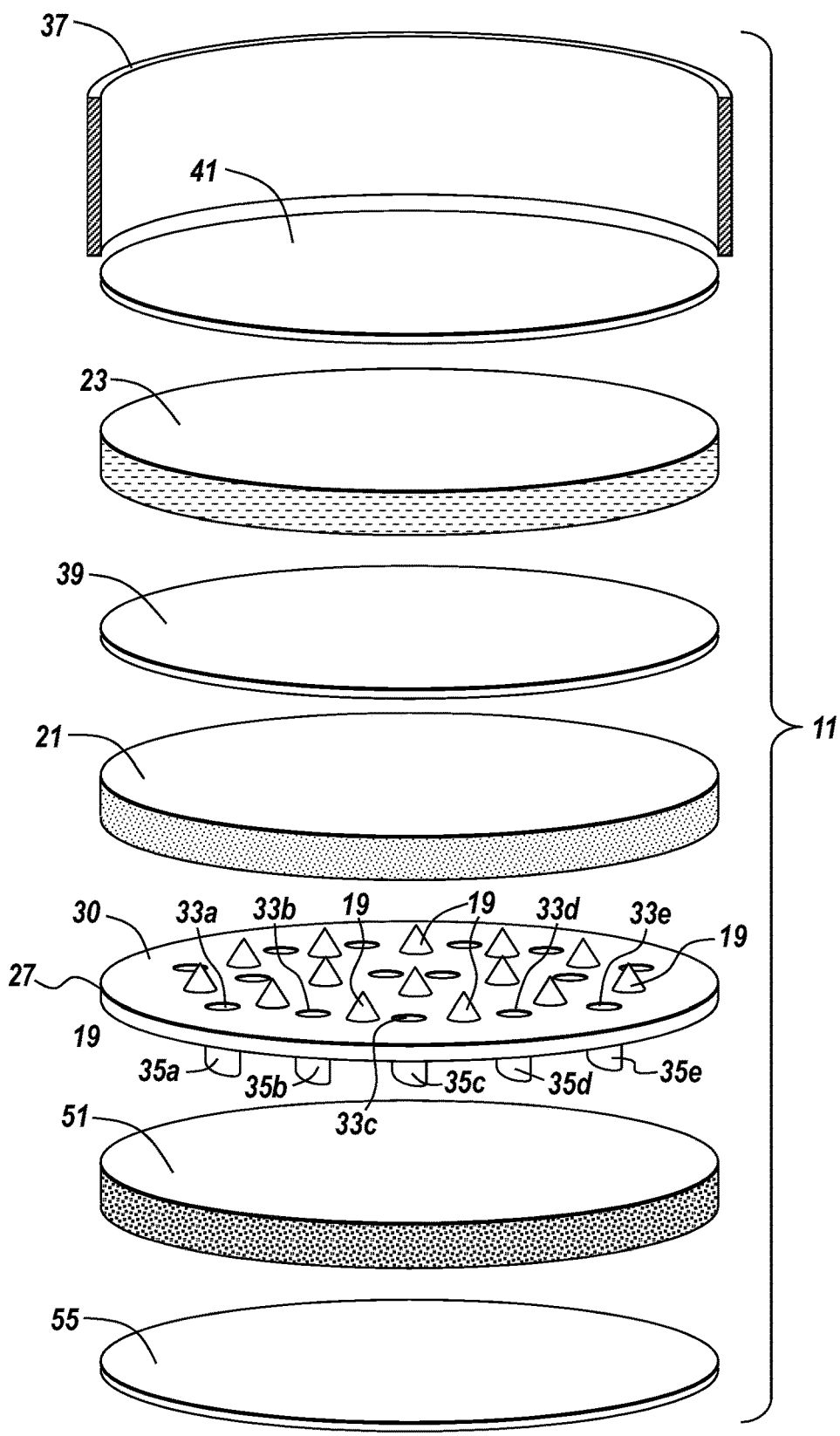
FIG. 2 depicts in exploded view a device having features of the present invention.

The collagen modifier compound 21 is one or more acetylation agents which is reactive with a natural dermal collagen. The collagen modifier compound 21 is depicted in FIG. 2 as a mass conforming substantially to the shape of the first compartment 15 with the understanding that it is a powder for reconstitution. The term "natural dermal collagen" refers to a collagen as it is normally and naturally found in the dermis layer of skin. A "modified collagen" refers to a collagen that has reacted with an acetylation agent and bears a higher net charge density due to the modification than the normal natural collagen. As used herein, an "acetylation agent" is a compound that transfers an acyl group to another nucleophile. Examples of acetylation agent include, without limitation, sulfonic acids, anhydrides, sulfonyl chlorides and acid chlorides. The acetylation agent includes compounds such as, without limitation, maleic anhydride, succinic anhydride, glutaric anhydride, citraconic anhydride, methyl succinic anhydride, itaconic anhydride, methyl glutaric anhydride, dimethyl glutaric anhydride, phthalic anhydride, oxalyl chloride, malonyl chloride, chlorosulfonylacetyl chloride, chlorosulfonylbenzoic acid, 4-chloro-3-(chlorosulfonyl)-5-nitrobenzoic acid, 3-sulfobenzoic acid, 3,5-dicarboxybenzenesulfonyl chloride, acetic anhydride, chloroacetic anhydride, propionic anhydride, butyric anhydride, isobutyric anhydride, isovaleric anhydride, hexanoic anhydride, acetyl chloride, propionyl chloride, dichloropropionyl chloride, butyryl chloride, isobutyryl chloride, valeryl chloride, ethane sulfonyl chloride, methane sulfonyl chloride, 1-butane sulfonyl chloride, 4, 6-diamino-2-methylthiopyrimidine-5-sulfonic acid and mixtures and combinations thereof. Several acetylation agents form reaction products with collagen which modify the collagen to increase the hydration of the collagen and/or elasticity of the collagen. The greater hydration of the collagen and/or elasticity of the collagen creates a fullness of the dermis which softens the appearance of lines and wrinkles. One acetylation agent featured in the present application is glutaric anhydride. The collagen modifier compound 21 is held as a powder for reconstitution. The collagen modifier compounds degrade in solution.

The reconstitution liquid 23 is in the nature of a sterile solution for injection which upon combining with the collagen modifier compound 21 forms a hydrated formulation. The reconstitution liquid is depicted in FIG. 2 as conforming to the shape of the second compartment 17 with the understanding that it is a liquid and therefore would not have such a free standing shape. The hydrated formulation holds the collagen modifier compound as a dissolved molecular species. The dissolved molecular species is unstable and needs to be administered within a short period of time. One preferred hydrated formulation comprises 1 to about 100 mg/ml glutaric anhydride in a buffered solution of pH 8 to about pH 10 normal saline.

Returning now to FIGS. 1 and 2, the injection means 13 is for receiving a collagen modifier compound in a hydrated formulation and transporting the hydrated formulation to a collagen site across the epidermal layer of the skin to react with endogenous collagen of the dermis. The injection means 13 has a sheet 27 having an administration side 29, a formulation side 31 and openings 33. As depicted and can best be seen in FIG. 2, the sheet 27 is generally circular in shape, however, it may have any shape including shapes which follow the contours of facial features. The administration side 29 has one or more needles 35a-35e in communication with the openings 33a-33e for transporting a hydrated formulation to the collagen site. As depicted, the administration side 29 has hollow cylindrical needles 35a-35e. However, the administration side may carry injection elements of different forms. By way of example, without limitation, the needles may comprise of solid or hollow forms or semi-hollow forms. The injection elements may comprise triangular, semicircular or rectangular wedge forms which open the epidermis and create a passage to the collagen site in the dermis.

Microneedle assemblies are commercially available through a variety of vendors including by way of example, without limitation, AdminMed (nanoBioSciences LLC) of Sunnyvale, Calif., and Procter Gamble, Cincinnati, Ohio and FujiFilm of Japan. The needles 35a-35e of the array are constructed and arranged to administer a dose into the dermis. The length of the needles of array is about 0.5 mm to about 1.0 mm.

The formulation side 31 is part of a first compartment 15 or is in fluid communication with a first compartment 15. The first compartment 15 is for holding a hydrated formulation and at least one of a collagen modifier compound 21 and a reconstitution liquid 23. The hydrated formulation is formed when the collagen modifier compound 21 is combined with the reconstitution liquid 23. First compartment 15 is formed by a generally cylindrical wall 37 which is welded or glued or molded with the sheet 27. Although described as generally cylindrical, wall 37 make take any shape of form. An internal membrane 39 welded, glued or molded with cylindrical wall 37 completes the enclosure. The first compartment is in fluid communication with the openings 33a -33e (additional openings are depicted in FIG. 2 but are not denoted with numerals to simplify the depiction) or constructed and arranged to form communication with the openings. As depicted, first compartment 15 holds a collagen modifier compound 21 and second compartment 17 holds a reconstitution liquid 23. The relative positions of the collagen modifier compound 21 and reconstitution liquid 23 can be reversed.

The second compartment 17 is for holding at least one of a collagen modifier compound 21 or a reconstitution liquid 23, whichever is not held in the first compartment 15. Combining the collagen modifier compound and the reconstitution liquid 23 forms a hydrated formulation which can be held in second compartment 17 and/or first compartment 15. Second compartment 17 is formed by the generally cylindrical wall 37, internal membrane 39 and a cover 41. Cover 41 is glued or welded to or integrally molded with the cylindrical wall 37.

Communication mean 19, for placing the first compartment 15 in fluid communication with a second compartment 17, is in the nature of one or more valves [not shown], a breakable seal or a breakable membrane or features or elements to break a seal or membrane, such as the knife projections depicted. As depicted, the communication means 19 and internal membrane 39 cooperate to separate the reactive collagen modifier compound 21 in first compartment 15 from the reconstitution liquid 23 held in second compartment 17. Upon activation of the communication means 19, knife projections disrupt the internal membrane 39. The communication means 19 may further comprise cutters and/or puncture elements, for example, projections protruding from the formulation side of the sheet which disrupt the integrity of the membrane or bending the device 11 or by pressing on membrane 39 directly or through the second compartment 17. Communication means 19 may also work with sonication elements or comprise sonication elements which when activated disrupt the breakable seal and/or membrane 39.

At least one of the first compartment 15 and second compartment 17 is collapsible to propel a hydrated formulation through the openings 33a-33e. The cylindrical wall 37, or parts thereof is made of a flexible plastic which can be collapsed to reduce the volumes of the first compartment 15 and second compartment 17.

The device 11 features at least one of the first compartment 15 and the second compartment 17 having window means to allow a user to view the hydrated formulation to ensure reconstitution of the collagen modifier compound. For example, without limitation, cylindrical wall 37 is comprised of clear plastic. In the alternative or in addition, cover 41 can be formed of a clear plastic. For example, without limitation, the first compartment 15 and/or the second compartment 17 is constructed and arranged with a clear plastic portion which allows the hydrated formulation to be viewed and monitored for the presence of undissolved collagen modifier compound.

Device 11 has a pad 51 fixed to the administration side 29 of said sheet 27. The pad 51 has serve a pretreatment agent, medicament and/or a skin marker. The medicament is for pretreating skin prior to administration of the hydrated formulation. For example, without limitation, the medicament may comprise conditioning agents, disinfecting agents, numbing agents and agents which render the skin more receptive to the collagen modifier compound 21. One pretreatment agent is a slightly alkaline buffer solution which is applied for 30 seconds to two minutes to bring the tissue pH to about 7.5 to 9.5. The pretreatment deprotonates free amines on proteins associated with the skin. The skin marker is a removable dye or coloring agent for marking the outline of the site of administration. As the user of the device, for example, without limitation, a health practitioner or cosmetician or the subject themselves administers the collagen modifier composition in the hydrated formulation, the individual can track the sites of administration to prevent missing locations and reapplication to the same location.

The pad 51 is held in a third compartment 53. The third compartment 53 is formed by cylindrical wall 37 and a base element 55. Base element 55 seals the openings 33a-33e to isolate the pretreatment agent from the collagen modifier compound 21 or a further seal or membrane is used [not shown] to isolate the collagen modifier compound in the first compartment 15. The pad 51 is exposed by removing base element 55, or portions thereof, or the cylindrical wall 37 proximal to the pad 51. Cylindrical wall 37 and/or base element 57 may have scoring to allow the separation of removable portions or be secured by glue which permits pulling apart.

Figure 3:
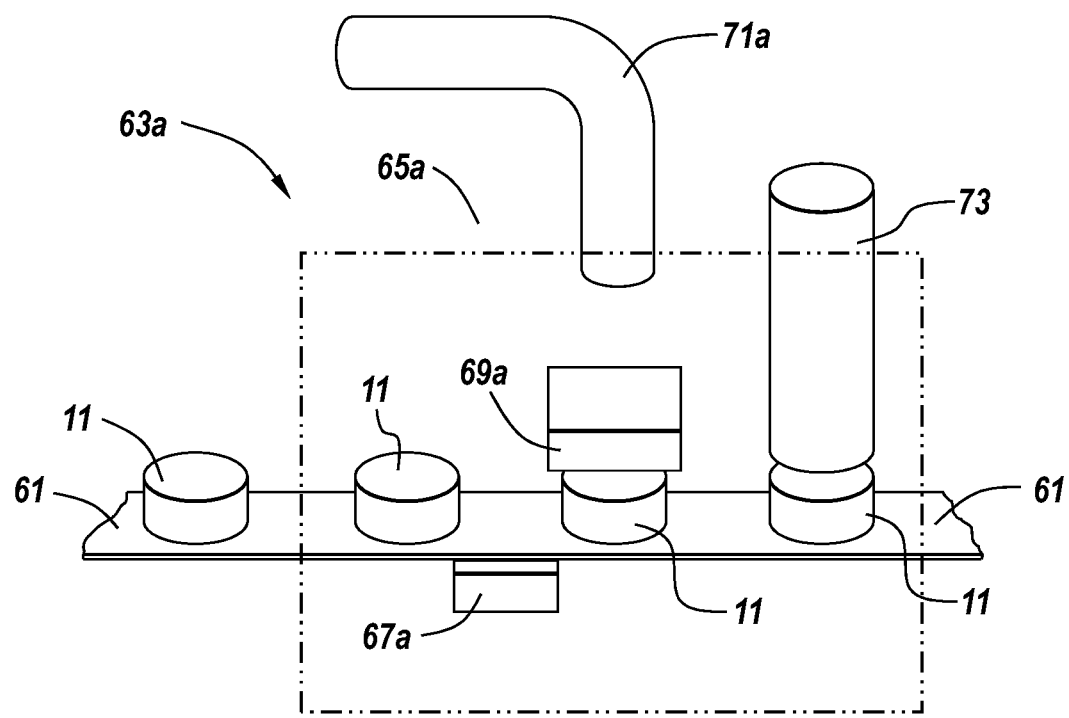
FIG. 3 depicts a dispensing apparatus and devices having features of the present invention.
Figure 4:
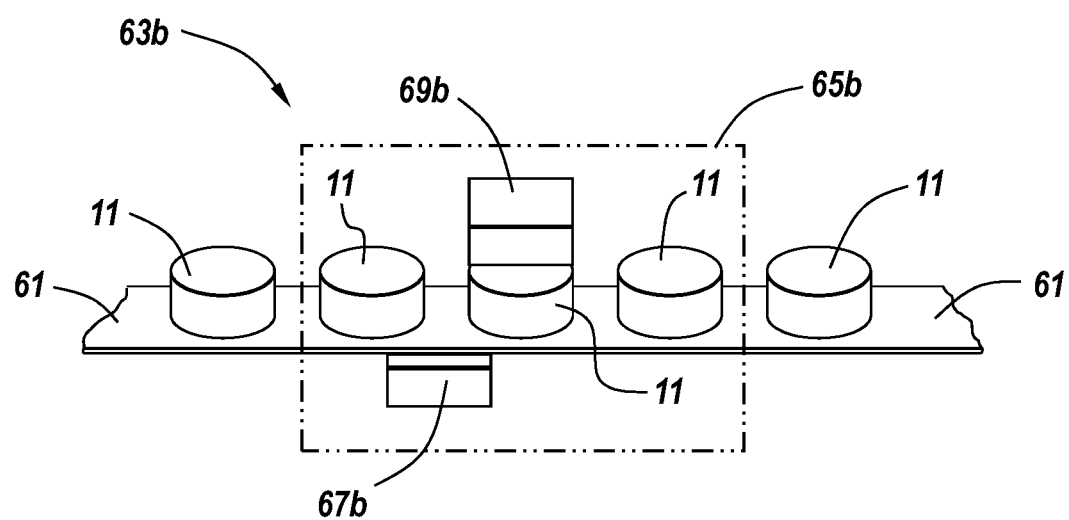
FIG. 4 depicts a dispensing apparatus and devices having features of the present invention.

Turning now to FIGS. 3 and 4, a plurality of devices is depicted on a strip 61. The strip 61 is received in a dispensing apparatus generally designated by the numeral 63a in FIGS. 3 and 63b in FIG. 4.

The dispensing apparatus 63a of FIGS. 3 and 63b of FIG. 4 is constructed and arranged to receive a plurality of devices 11 on strips 61. Each dispensing apparatus 63a and 63b facilitate the administration of the hydrated formulation by holding the devices 11 for easy manipulation by a user and/or processing the collagen modifier compound 21 and reconstitution liquid 23 to form a hydrated formulation and/or applying the injection means 13 to the skin.

Turning now to FIG. 4, the dispensing apparatus 63b, has a housing 65b which housing 65b holds a motor assembly 67b and a sonication element 69b. Motor assembly 67b has strip engagement features, for example, without limitation, cooperating holes and pins or gears, gripping surfaces and the like, which allow a motor assembly 67b to engage the strip 61 and advance the strip through the housing 65b. In the alternative, levers and other mechanical elements manually operated are used to advance the strip 61.

Each device 11 passing through the housing 65b is processed to form a hydrated formulation. Dispensing apparatus 63b has a sonication element 69b which disrupts the membrane 39 separating the first compartment 15 from the second compartment 17 and promotes the dissolution of the collagen modifier compound. The dispensing device 63b may also have sensors [not shown] which monitor the first compartment 15 and/or second compartment 17 for such dissolution.

Advancement of the strip 61 presents the device 11 for use by the user, health practitioner or cosmetician. The user removes the device 11 from the strip 61 or while the device 11 is part of the strip, applies the rehydrated formulation to the subject.

Turning now to FIG. 3, dispensing apparatus 63a has a housing 65a which housing includes a handle 71a. The housing 65a holds a motor assembly 67a and a sonication element 69a. Motor assembly 67a has strip engagement features, for example, without limitation, cooperating holes and pins or gears, gripping surfaces and the like, which allow a motor assembly 67a to engage the strip 61 and advance the strip through the housing 65a. In the alternative, levers and other mechanical elements manually operated are used to advance the strip 61.

Each device 11 passing through the housing 65a is processed to form a hydrated formulation. Dispensing apparatus 63a has a sonication element 69a which disrupts the membrane 39 separating the first compartment 15 from the second compartment 17 and promotes the dissolution of the collagen modifier compound. The dispensing device 63a may also have sensors [not shown] which monitor the first compartment 15 and/or second compartment 17 for such dissolution. The dispensing apparatus 63a has a press element 73 for pressing the device 11 such that the injection means 13 is pressed into the skin and the first compartment 15 and/or second compartment 17 is collapsed to propel the hydrated formulation into the collagen site. Press element 73 can be manually operated or powered by solenoid or motors [not shown].

The dispensing apparatus 63a and 63b depicted in FIGS. 3 and 4 may also process the strips to remove the third compartment 51.

Embodiments of the present method will now be described with respect to the device 11 and the dispensing apparatus 63a and 63b and the manner of using such devices 11. In operation, a device 11 is provided for administering a collagen modifier compound 21 having injection means 13, a first compartment 15, a second compartment 17, communication means 19, a collagen modifier compound 21, and a reconstitution liquid 23. The injection means 13 is for receiving a collagen modifier compound 21 in a hydrated formulation and transporting the hydrated formulation to a collagen site across the epidermal layer of the skin to react with endogenous collagen of the dermis. The injection means 13 has a sheet 27 having an administration side 29, a formulation side 31 and openings 33. The administration side 29 has one or more needles 35 in communication with the openings 33 for transporting a hydrated formulation to the collagen site. The formulation side 31 forms a first compartment 15 or is in fluid communication with a first compartment 15. The first compartment 15 is for holding a hydrated formulation and at least one of a collagen modifier compound 21 and a reconstitution liquid 23. The second compartment 17 is for holding at least one of a collagen modifier compound 21, a reconstitution liquid 23 and a hydrated formulation. At least one of the first compartment 15 and second compartment 17 is collapsible to propel a hydrated formulation through the openings 33. The communication means 19 is for placing the first compartment 15 in fluid communication with the second compartment 17 to allow a collagen modifier compound 21 to become hydrated with a reconstitution liquid 23 to form a hydrated formulation for administration. The collagen modifier compound 21 held in one of the first compartment 15 and the second compartment 17. The reconstitution liquid 23 is held in one of said first compartment 15 and the second compartment 17 not holding the collagen modifier compound 21. The collagen modifier compound 21 and reconstitution liquid 23 form a hydrated formulation for administration through the epidermis upon activation communication means 19. The injection means 13 is for placing openings 33 proximal to a collagen site upon pressing the administration side against the skin, and the at least one of the first compartment 15 and second compartment 17 for collapsing propelling hydrated formulation to the collagen site.

The method further comprises the step of forming a hydrated formulation by activating the communication means 19, combining the collagen modifier compound 21 with the reconstitution liquid 23. The activation of the communication means 19 can be performed manually or with the aid of a dispensing apparatus 63a or 63b. The dispensing apparatus 63a and 63b feature sonication elements 69a and 69b to disrupt the membrane 39 and promote dissolution of the collagen modifier compound 21. Sensors [not shown] determine when the collagen modifier compound 21 is in solution. In the alternative or in addition, the user can inspect the first compartment 15 and/or the second compartment 17 through windows provided in the cylindrical wall 37.

The user presses the administration side 29 of the sheet 27 on the skin at the site of administration and pressing the one or more needles 35 into the skin. This step can be performed manually or with the aid of a dispensing apparatus 63a. In using dispensing apparatus 63a, the user grips the handle 71a and positions the press element 73 over the site of administration, and presses the administration element against the skin. Pressing the device 11 against the skin collapses the at least one of the first compartment 15 and second compartment 17 to propel said hydrated formulation to the site.

The pressing of the device 11 into the skin is optionally preceded by pretreating the administration site with medicaments, pretreatment agents, marking agents and anesthetic agents held in the pad 51. The third compartment 53 is opened prior to pretreatment or pressing steps.

One embodiment of the method features at least one of said first compartment and said second compartment having window means to allow a user to view the hydrated formulation to ensure reconstitution of the collagen modifier compound and further comprises the step of viewing the hydrated formulation prior to propelling the hydrated formulation to the site. The pad 51 with marking agents leaves an indicia or marking showing where the hydrated formulation has been applied. The user can use the indicia to determine a next site for administration.

One embodiment of the method features a pad 51 held in a third compartment. The third compartment has means for exposing the pad and the method further comprising the step of exposing the pad 51 and pressing the pad 51 against the site to pretreat the site.

Embodiments of the present device 11, dispensing apparatus 63a and 63b and methods facilitate the use of collagen modifier compound which have a short half-life in solution. It allows the user to administer to sites sequentially in rapid succession minimizing discomfort to the subject experiencing the treatment and efficiently utilizing time and effort.

Thus we have described the invention with respect to the best mode of making and using its features with the understanding that the invention is subject to modification and alteration without departing from the teaching herein. Therefore, the present invention should not be limited to the detailed description but should encompass the subject matter recited in the claims that follow and their equivalents.

We claim:

1. A device for administering a collagen modifier compound comprising:
   a. injection means for receiving a collagen modifier compound in a hydrated formulation and transporting said hydrated formulation to a collagen site across the epidermal layer of the skin to react with endogenous collagen, said injection means having a sheet having an administration side, a formulation side and openings, said administration side having one or more needles in communication with said openings for transporting said hydrated formulation to said collagen site, said formulation side forming a first compartment or in fluid communication with a first compartment;
   b. a first compartment for holding hydrated formulation and at least one of a collagen modifier compound and a reconstitution liquid, said first compartment in fluid communication with said openings or constructed and arranged to form communication with said openings;
   c. a second compartment for holding at least one of a collagen modifier compound, a reconstitution liquid and a hydrated formulation, at least one of said first compartment and second compartment collapsible to propel a hydrated formulation through said openings;
   d. communication means for placing said first compartment in fluid communication with said second compartment to allow a collagen modifier compound to become hydrated with a reconstitution liquid to form a hydrated formulation for administration;
   e. a collagen modifier compound held in one of said first compartment or said second compartment;
   f. a reconstitution liquid held in one of said first compartment or said second compartment not holding said collagen modifier compound;
   said collagen modifier compound and reconstitution liquid for forming a hydrated formulation for administration through the epidermis upon activation communication means and said injection means for placing openings in proximal to a collagen site upon pressing the administration side against the skin, said at least one of said first compartment and second compartment for collapsing propelling hydrated formulation to said collagen site.

2. The device of claim 1 wherein at least one of said first compartment and said second compartment have window means to allow a user to view the hydrated formulation to ensure reconstitution of the collagen modifier compound.

3. The device of claim 1 further comprising a pad fixed to said administration side of said sheet.

4. The device of claim 3 wherein said pad has a medicament, said medicament for pretreating skin prior to administration of said hydrated formulation.

5. The device of claim 4 wherein said pad is held in a third compartment.

6. The device of claim 5 wherein said third compartment has means for exposing said pad.

7. The device of claim 3 wherein said pad has a skin marker for marking the outline of the site of administration.

8. The device of claim 1 further comprising strip means for maintaining said device a one of a plurality in a strip for dispensing.

9. The device of claim 8 wherein said strip means is received in a dispensing apparatus.

10. The device of claim 9 further comprising a dispensing apparatus.

11. The device of claim 10 wherein said dispensing apparatus has sonication means for promoting the dissolution of the collagen modifier compound.

12. The device of claim 10 wherein said dispensing apparatus has compression means for compressing said at least one of said first and second compartments to administer said collagen modifying compound.

13. A method of administering a hydrated formulation comprising the steps of:
   a. providing a device for administering a collagen modifier compound having:
      i. injection means for receiving a collagen modifier compound in a hydrated formulation and transporting said hydrated formulation to a collagen site across the dermis layer of the skin to react with endogenous collagen, said injection means having a sheet having an administration side, a formulation side and openings, said administration side having one or more needles in communication with said openings for transporting said hydrated formulation to said collagen site, said formulation side forming a first compartment or in fluid communication with a first compartment;
      ii. a first compartment for holding at least one of a collagen modifier compound, a hydrated formulation and a reconstitution liquid, said first compartment in fluid communication with said openings or constructed and arranged to form communication with said openings;
      iii. a second compartment for holding at least one of a collagen modifier compound, a reconstitution liquid and a hydrated formulation, at least one of said first compartment and second compartment collapsible to propel a hydrated formulation through said openings;
      iv. communication means for placing said first compartment in fluid communication with said second compartment to allow a collagen modifier compound to become hydrated with a reconstitution liquid to form a hydrated formulation for administration;
      v. a collagen modifier compound held in one of said first compartment or said second compartment;
      vi. a reconstitution liquid held in one of said first compartment or said second compartment not holding said collagen modifier compound;
      said collagen modifier compound and reconstitution liquid for forming a hydrated formulation for administration through the dermis upon activation communication means and said injection means for placing openings in proximal to a collagen site upon pressing the administration side against the skin, said at least one of said first compartment and second compartment for collapsing propelling hydrated formulation to said collagen site.
   b. forming a hydrated formulation by activating said communication means and combining the collagen modifier compound with said reconstitution liquid; and,
   c. pressing said administration side of said sheet on the skin at the site of administration and pressing said one or more needles into the skin;
   d. collapsing said at least one of said first compartment and second compartment to propel said hydrated formulation to said site.

14. The method of claim 13 wherein at least one of said first compartment and said second compartment have window means to allow a user to view the hydrated formulation to ensure reconstitution of the collagen modifier compound and further comprising the step of viewing the hydrated formulation prior to propelling the hydrated formulation to said site.

15. The method of claim 13 further comprising a pad fixed to said administration side of said sheet wherein said pad has a medicament, said medicament for pretreating skin prior to administration of said hydrated formulation said method comprising the step of pretreating the skin by holding said pad at the site.

16. The method of claim 15 wherein said pad is held in a third compartment and said third compartment has means for exposing said pad said method further comprising the step of exposing said pad.

17. The method of claim 15 wherein said pad has a skin marker for marking the outline of the site of administration and further comprising the step of monitoring the administration by marking the skin.

18. The method of claim 17 further comprising the step of aligning the mark on the skin with a subsequent application of hydrated formulation.

19. The method of claim 13 wherein said step of forming a hydrated formulation comprises sonification.

20. The method of claim 13 wherein said device is held in a strip means for maintaining said device a one of a plurality in a strip for dispensing apparatus.

21. The method of claim 13 wherein said strip means is received in a dispensing apparatus.

22. The method of claim 21 wherein said dispensing apparatus has sonication means for promoting the dissolution of the collagen modifier compound.

23. The method of claim 21 wherein said dispensing apparatus has compression means for compressing said at least one of said first and second compartments to administer said collagen modifying compound.

24. A dispensing apparatus for receiving a device for administering a collagen modifier compound, said dispensing apparatus having device holding means and said device having:
  i. injection means for receiving a collagen modifier compound in a hydrated formulation and transporting said hydrated formulation to a collagen site across the dermis layer of the skin to react with endogenous collagen, said injection means having a sheet having an administration side, a formulation side and openings, said administration side having one or more needles in communication with said openings for transporting said hydrated formulation to said collagen site, said formulation side forming a first compartment or in fluid communication with a first compartment;
  ii. a first compartment for holding at least one of a collagen modifier compound, a hydrated formulation and a reconstitution liquid, said first compartment in fluid communication with said openings or constructed and arranged to form communication with said openings;
  iii. a second compartment for holding at least one of a collagen modifier compound, a reconstitution liquid and a hydrated formulation, at least one of said first compartment and second compartment collapsible to propel a hydrated formulation through said openings;
  iv. communication means for placing said first compartment in fluid communication with said second compartment to allow a collagen modifier compound to become hydrated with a reconstitution liquid to form a hydrated formulation for administration;
  v. a collagen modifier compound held in one of said first compartment or said second compartment;
  vi. a reconstitution liquid held in one of said first compartment or said second compartment not holding said collagen modifier compound;
  said collagen modifier compound and reconstitution liquid for forming a hydrated formulation for administration through the dermis upon activation communication means and said injection means for placing openings in proximal to a collagen site upon pressing the administration side against the skin, said at least one of said first compartment and second compartment for collapsing propelling hydrated formulation to said collagen site;
  said dispensing apparatus having activation means for activating said communication means.

25. The dispensing apparatus of claim 24 further comprising means for collapsing said at least one of said first compartment and said second compartment propelling said hydrated formulation through said openings.

26. The dispensing apparatus of claim 24 further comprising sonication means.

* * * * *